(12) United States Patent
Sharkey et al.

(10) Patent No.: US 6,177,556 B1
(45) Date of Patent: Jan. 23, 2001

(54) HUMAN SCF, A SPLICE VARIANT THEREOF, ITS PHARMACEUTICAL USE

(75) Inventors: Andrew Mark Sharkey; Stephen Kevin Smith, both of Cambridge; Kimberley Anne Dellow, London, all of (GB)

(73) Assignee: Applied Research Systems ARS Holdings N.V., Curacao (NL)

( * ) Notice: Under 35 U.S.C. 154(b), the term of this patent shall be extended for 0 days.

(21) Appl. No.: 08/836,252

(22) PCT Filed: Oct. 31, 1995

(86) PCT No.: PCT/GB95/02547

§ 371 Date: Jul. 31, 1997

§ 102(e) Date: Jul. 31, 1997

(87) PCT Pub. No.: WO96/14410

PCT Pub. Date: May 17, 1996

(30) Foreign Application Priority Data

Nov. 4, 1994 (GB) .................................................. 9422293
Apr. 28, 1995 (GB) .................................................. 9508618

(51) Int. Cl.$^7$ ............................ C07H 21/04; C07K 14/52
(52) U.S. Cl. ................. 536/23.5; 435/320.1; 435/252.3; 435/69.5; 530/351; 514/44; 514/2; 424/85.1
(58) Field of Search ........................ 536/23.5; 435/69.5, 435/320.1, 252.3; 530/351; 424/85.1; 514/44

(56) References Cited

U.S. PATENT DOCUMENTS 5,885,962 * 3/1999 Lu ........................................ 530/380

FOREIGN PATENT DOCUMENTS 0 423 980 A1   4/1991 (EP) .

OTHER PUBLICATIONS

Hill, J.A. et al., "Products of activated lymphocytes and macrophages inhibit mouse embryo development in vitro," *J. Immunol.* 139:2250–2254 (Oct. 1987).

Pampfer, S. et al., "Expression of Tumor Necrosis Factor–α (TNF α) Receptors and Selective Effect of TNFα on the Inner Cell Mass in Mouse Blastocysts," *Endocrinology* 134:206–212 (Jan. 1994).

Harvey, M.B. et al., "Insulin–like Growth Factor–1 Stimulates Growth of Mouse Preimplantation Embroyos In Vitro," *Molecular Reproduction and Development*, 31: 195–199 (Mar. 1992).

Arceci, R.J. et al., "Expression of CSF–1/c–fms and SF/c–kit mRNA during preimplantation mouse development,"*Chemical Abstracts 116* (23): 62 Abstract No. 116:228032m (1992).

Braude, P. et al., "Human gene expression first occurs between the four— and eight–cell stages of preimplantation development," *Nature 332* (6163): 459–461 (1988).

Flanagan, J.G. et al., "Transmembrane Form of the *kit* Ligand Growth Factor Is Determined by Alternative Splicing and Is Missing in the SI$^d$ Mutant," *Cell 64*:1025–1035 (1991).

Langley, K.E. et al., "Properties of Variant Forms of Human Stem Cell Factor Recombinantly Expressed in *Escherichia coli*," *Arch Biochem. Biophys. 311*(1):55–61 (May 1994).

Martin, F.H. et al., "Primary Structure and Functional Expression of Rat and Human Stem Cell Factor DNAs," *Cell 63*:203–211 (1990).

Sharkey, A. et al., "Expression of Messenger RNA for Kit–Ligand in Human Placenta: Localization by *in Situ* Hybridization and Identification of Alternatively Spliced Variants," *Mol. Endo. 6*(8): 1235–1241 (1992).

Sharkey, A.M. et al., "Stage–Specific Expression of Cytokine and Receptor Messenger Ribonucleic Acids in Human Preimplantation Embryos," *Biol. Reprod.* 53(4):974–981 (Oct. 1995).

Nishikawa et al, *Biochem. Biophys Res. Comm* 188(1) 1992, p 292–297.*

Lu et al, *Arch. Biochem. Biophys.* 298(1) 1992 p 150–158.*

Anderson et al, Cell Growth & Differentiation, vol. 2, 1991, p 373–78.*

The Cytokine Handbook, ed Cullard, 1994, p. 228–232.*

* cited by examiner

*Primary Examiner*—Garnette D. Draper
(74) *Attorney, Agent, or Firm*—Sterne, Kessler, Goldstein & Fox P.L.L.C.

(57) ABSTRACT

SCF which includes the following C-terminal sequence: Glu Ile Cys Ser Leu Leu Ile Gly Leu Thr Ala Tyr Lys Glu Leu Ser Leu Pro Lys Arg Lys Glu Thr Cys Arg Ala Ile Gln His Pro Arg Lys Asp or a C-terminal sequence which is substantially homologous thereto and its use in medicine, particularly in ensuring the correct development of preimplantation embryos.

8 Claims, 3 Drawing Sheets

```
               exon 3  ↓   new exon
           ATG GAT GTT TTG GAA ATC TGT TCA TTG TTG ATA GGG CTG ACG GCC
           met asp val leu glu ile cys ser leu leu ile gly leu thr ala TAT AAG GAA TTA TCA CTC CCT AAA AGG AAA GAA ACT TGC AGA GCA
           tyr lys glu leu ser leu pro lys arg lys glu thr cys arg ala ATT CAG CAT CCA AGG AAA GAC TGA CAG CTT TGA AAG AGA CCT GAT
           ile gln his pro arg lys asp END
                                       new exon    ↓   exon 4
           AAT GAT GCA AGT AGG AAC TTG CAT GTG CTT GAA CCA AGT CAT TGT
```

FIG. 1

FIG. 3

```
                -25                    -20
                 M  K  K  T  Q  T  W  I  L  T  C  I  Y  L  Q
      AAGCTTGCCTTTCCTTATGAAGAAGACACAAACTTGGATTCTCACTTGCATTTATCTTCAG        61

-10                       1                            10
        L  L  L  F  N  P  L  V  K  T  E  G  I  C  R  N  R  V  T  N
      CTGCTCCTATTTAATCCTCTCGTCAAAACTGAAGGGATCTGCAGGAATCGTGTGACTAAT        121

20                            30
        N  V  K  D  V  T  K  L  V  A  N  L  P  K  D  Y  M  I  T  L
      AATGTAAAAGACGTCACTAAATTGGTGGCAAATCTTCCAAAAGACTACATGATAACCCTC        181

40                            50
        K  Y  V  P  G  M  D  V  L  P  S  H  C  W  I  S  E  M  V  V
      AAATATGTCCCCGGGATGGATGTTTTGCCAAGTCATTGTTGGATAAGCGAGATGGTAGTA        241

60                            70
        Q  L  S  D  S  L  T  D  L  L  D  K  F  S  N  I  S  E  G  L
      CAATTGTCAGACAGCTTGACTGATCTTCTGGACAAGTTTTCAAATATTTCTGAAGGCTTG        301

80                            90
        S  N  Y  S  I  I  D  K  L  V  N  I  V  D  D  L  V  E  C  V
      AGTAATTATTCCATCATAGACAAACTTGTGAATATAGTGGATGACCTTGTGGAGTGCGTG        361

100                           110
        K  E  N  S  S  K  D  L  K  K  S  F  K  S  P  E  P  R  L  F
      AAAGAAAACTCATCTAAGGATCTAAAAAAATCATTCAAGAGCCCAGAACCCAGGCTCTTT        421

120                           130
        T  P  E  E  F  F  R  I  F  N  R  S  I  D  A  F  K  D  F  V
      ACTCCTGAAGAATTCTTTAGAATTTTTAATAGATCCATTGATGCCTTCAAGGACtTTGTA        481

140                           150
        V  A  S  E  T  S  D  C  V  V  S  S  T  L  S  P  E  K  D  S
      GTGGCATCTGAAACTAGTGATTGTGTGGTTTCTTCAACATTAAGTCCTGAGAAAGATTCC        541

160                           170
        R  V  S  V  T  K  P  F  M  L  P  P  V  A  A  S  S  L  R  N
      AGAGTCAGTGTCACAAAACCATTTATGTTACCCCCTGTTGCAGCCAGCTCCCTTAGGAAT        601

180   183
        D  S  S  S  S  N  S  K  Y  I  Y  L  I
      GACAGCAGTAGCAGTAATAGTAAGTACATATATCTGATTTAATGCATGCATGGCTCCAAT        661

TAGCACCTATAGGAGTATTGCATGGGCTTTCAAGGAAACTTCTACATTTATTATTATTGA        721

TACTGTTCTGTTACTGTTATTCCTTTTATGGTCTTCTTGAGACTTAAGTTTGTAGAATTA        781

AATTTCCCTAGAGCTGGAGATAATGTTTAGAGAATTAGG                             820
```

| SPECIFICITY | PRIMER | SEQUENCE 5'→3' | FRAGMENT SIZE (bp) | POSITION ON cDNA | REFERENCE (cDNA SEQUENCE) |
|---|---|---|---|---|---|
| HistRS | A | CCGCAGGTCGAGACAGC | | 518-534 | RABEN et al 1992 |
| | B | CAAACACCTTCTCGCGAA | | 791-773 | NUCLEIC ACIDS RES |
| | C | CTTCAGGGAGAGCGCGTGC | | 595-613 | 20:1075-1081 |
| | D | TCATCAGGACCCAGCTGTGC | 110 | 704-685 | |
| SCF | A | CAATGCGTGGACTATCTGCC | | 9-28 | MARTIN et al 1990 |
| | B | GTTCTAAATGAGACCCAAGT | | 1284-1264 | CELL |
| | C | AACAGCTAAACGGAGTCGCC | | 61-80 | 63:203-211 |
| | D | ACAGTGTTGATACAAGCCAC | 966 | 1027-1008 | |
| c-kit | A | GAAGTACAGTGGAAGGTTGTT | | 1681-1702 | YARDEN et al 1987 |
| | B | CATCGGCCACTAAAGTGTGCT | | 3105-3086 | EMBO |
| | C | GGTTGTTGAGGCAACTGCTTA | | 1827-1847 | 6:3341-3351 |
| | D | GGTGACCCAAACACTGATTC | 1148 | 2975-2955 | |

HUMAN SCF, A SPLICE VARIANT THEREOF, ITS PHARMACEUTICAL USE

FIELD OF THE INVENTION

The present invention relates to a novel human stem cell factor (SCF) protein, DNA sequences coding for this protein, its use in therapy, particularly in in vitro fertilisation, as well as pharmaceutical formulations comprising such a protein.

BACKGROUND OF THE INVENTION

Successful embryo implantation requires correct development of the pre-implantation embryo, resulting in a hatched blastocyst which is able to implant into receptive endometrium. A considerable body of data has been collected which supports the idea that soluble growth factors, if secreted by the uterine epithelium, act directly on the embryo to control this process (Pampfer, S. et al, Bioessays, 13: 535–540 (1991); Tartakousky, B., and Ben Yair, E., Development Biology, 146: 345–352 (1991); Anderson, E. D., J. Cellular Biochem., 53: 280–287 (1993); and Schultz, G. A. and Hevner, S., Mutat. Res., 296: 17–31 (1992)).

In addition, developing embryos have been shown to produce a variety of cytokines which may act in an autocrine fashion on the endometrium to influence its receptivity. Examples of growth factors shown to be produced by human embryos include IL-1, IL-6, CSF-1 and TNF-α (Zolti et al, Fertil. Steril., 56 (1991) 265–272 and Witkin et al, J. Reprod. Immunol., 19 (1991) 85–93). TNF-α has been shown to be present in culture medium of human embryos up to the morula-st-age, but not that from the blastocyst (Lachappelle et al, Human Reproduction, 8: 1032–1038 (1993)). Production of cytokines by the embryo may therefore be regulated in a stage-specific manner.

Data on the possible direct effects of cytokines on embryos have come primarily from experiments in mice where many cytokines have been shown to affect the development of pre-implantation embryos in vitro. IFN-γ and CSF-1, at physiological concentrations, inhibit the number of embryos developing to the blastocyst stage (Hill et al, J. Immunol., 139 (1987) 2250–2254). TNF-α has also been shown to have more subtle effects. Although TNF-α has no apparent effect on rates of blastocyst formation, it appears to specifically inhibit proliferation of cells contributing to the inner cell mass (ICM), which results in blastocysts with a reduced ICM (Pampfer et al, Endocrinology, 134: 206–212 (1994)).

Other growth factors also have specific effects on ICM cells. For instance, insulin-like growth factors 1 and 2 stimulate ICM proliferation, whereas leukaemia inhibitory factor (LIF) inhibits their differentiation (Harvey et al, Mol. Reprod. Dev., 31 (1992) 195–199).

It has been observed, in mouse systems, that embryos cultured in vitro lag in development compared to in vivo controls, and exhibit lower pregnancy rates after embryo transfer (Bowman, P. and McLaren, A., J. Embryol. Exp. Morphol., 24: 203–207 (1970)). Thus, a better understanding of the role of growth factors in development could lead to improved in vitro culture conditions and enhance the outcome in human IVF programs.

Stem cell factor (SCF) is a growth factor related in structure to CSF-1, and acts through the c-kit tyrosine kinase receptor. In bone marrow, SCF and CSF-1 act synergistically to promote proliferation and differentiation of stem cells into macrophage colonies.

EP-A-0423980 discloses the nucleic acid sequence of human SCF, and discusses potential uses of SCF in conditions requiring stimulation of cell proliferation, particularly blood cells.

In mouse, c-kit has been shown to be expressed throughout pre-implantation development (Arceci et al (1992)). We have now shown that the same is true in human embryos. At certain stages the human embryos also express SCF mRNA, suggesting that this growth factor may act in an autocrine fashion. This is in contrast to mouse, where no expression of SCF was detected in pre-implantation embryos (Arceci et al (1992)).

The full length SCF transcript consists of eight exons (Martin, F. H. et al, Cell, 63: 203–211 (1990)), which paper also discloses a variant form of SCF. A splice-variant of SCF has also been described which arises by virtue of the loss of exon 6 (Flanagan et al, Cell, 63: 1025–1035 (1991)).

SUMMARY OF THE INVENTION

There has now been found a further, novel, splice-variant which appears to arise due to the inclusion of a novel exon consisting of 155 base pairs between exons 3 and 4. This also results in a frameshift, and codes for a species of SCF comprising 33 novel amino acids following exon 3, before terminating at an in frame stop codon which now appears in exon 4 due to the frameshift.

DESCRIPTION OF THE PREFERRED EMBODIMENTS

Thus, the present invention provides SCF which includes the following C-terminal sequence (SEQ ID NO:1):

```
Glu Ile Cys Ser Leu Leu Ile Gly Leu Thr Ala Tyr Lys
Glu Leu Ser Leu Pro Lys Arg Lys Glu Thr Cys Arg Ala
Ile Gln His Pro Arg Lys Asp
``` or a sequence which is substantially homologous thereto.

Preferably, the novel SCF of the invention comprises the first 39 amino acids of full length SCF (not including any signal sequence) followed by the above-noted 33 new amino acids. In one embodiment the novel SCF of the invention has a sequence at positions 1–39 substantially homologous to that shown in FIG. 2.

At the amino acid level, a protein sequence may be regarded as substantially homologous to another protein sequence if a significant number of the constituent amino acids exhibit homology. At least 40%, 50%, 60%, 70%, 80% 90%, 95% or even 99%, in increasing order of preference, of the amino acids may be homologous.

Thus, the alternative splicing mechanism can result in the production of a novel SCF in human embryos. Therefore, the novel SCF of the invention can be used in the treatment of pre-implantation embryos to ensure correct differentiation and development prior to implantation in a subject.

In addition, the invention also provides a DNA sequence coding for a protein of the invention which sequence includes a sequence Substantially homologous to (SEQ ID NO:2):

```
GAA ATC TGT TCA TTG TTG ATA GGG CTG ACG GCC TAT AAG

GAA TTA TCA CTC CCT AAA AGG AAA GAA ACT TGC AGA GCA

ATT CAG CAT CCA AGG AAA GAC TGA
``` and includes all other nucleic acid sequences which, by virtue of the degeneracy of the genetic code, also code for the given amino acid sequence or which are substantially homologous to such a sequence.

Sequences having substantial homology may be regarded as those which will hybridise to the nucleic acid sequence shown in FIG. 2 under stringent conditions (for example, at 35 to 65° C. in a salt solution of about 0.9M).

DNA constructs comprising DNA sequences of the invention form another aspect of the present invention.

As discussed herein, the protein of the invention is useful in treating embryos to ensure correct development prior to implantation. SCF has been shown to act by binding to the transmembrane receptor c-kit. Furthermore, we have shown that human embryos express c-kit throughout most stages of pre-implantation embryo development.

Thus, in further aspects, the present invention provides:

(a) a method for ensuring the correct development of a pre-implantation embryo which comprises the step of administering the SCF of the present invention to a pre-implantation embryo (and preferably a human embryo); and (b) a method for ensuring the correct development of a human pre-implantation embryo which comprises the step of administering SCF to a human pre-implantation embryo. In this method, the SCF used can be any of the naturally occurring forms, including previously described variants (Martin et al, supra and Flanagan et al, supra), as well as the novel variant described herein.

In addition, the invention also provides the use of SCF in the manufacture of a medicament for use in ensuring correct development in human pre-implantation embryos. Again, any form of SCF can be used to produce a suitable medicament.

The medicament is preferably presented in the form of a pharmaceutical formulation comprising the protein of the invention together with one or more pharmaceutically acceptable carriers and/or excipients. Such pharmaceutical formulations form a yet further aspect of the present invention. Such pharmaceutical formulations represent one way in which the SCF can be used in the methods described above.

BRIEF DESCRIPTION OF THE DRAWINGS

The invention will now be described by means of the following examples, which examples should not be construed as in any way limiting the present invention. The examples refer to the following figures which show:

FIG. 1: the sequence of the novel exon (SEQ ID NO:3) and the predicted amino acid sequence (SEQ ID NO:4);

FIG. 2: the sequence of human SCF (SEQ ID NO:5 and (SEQ ID NO:6);

FIG. 3: agarose gel showing the products of nested RT-PCR amplification on RNA from human embryos. Each panel shows the products of amplification with primers specific for different cDNA targets. Amplified cDNAs from different embryos were loaded in each lane. Lanes are labelled according to CDNA labels in Table 1 (below). Additional samples were: lane p, first trimester trophoblast; lane q, CDNA from 200 BeWO cells; lane r, 10 ng human genomic DNA; and lane s, no input CDNA, as a negative control. DNA molecular weight markers were a 123 base pair ladder loaded in lane i. The sizes of the expected PCR products are shown in bp.

TABLE 1

Human embryo cDNAs and controls

| name | stage of development |
|------|---------------------|
| a | 2 cell |
| b | 3 cell |
| c | 4 cell |
| d | 6 cell |
| e | 8 cell |
| f | morula |
| g | blastocyst |
| h | culture supernatant for a to g |
| j | three pooled blastocysts |
| k | culture supernatant for j |
| l | 2 × 6 cell and 1 × 8 cell |
| m | culture supernatant for l |
| n | 1 × 4 cell and 1 × 6 cell |
| o | culture supernatant for n | samples a to h are from the same donor.

FIG. 4: primers used for RT-PCR, outer pain A and B, inner pain C and D.

EXAMPLES

Example 1

Embryo Culture and RNA Extraction

Crypopreserved human embryos which had been fertilised as part of an IVF program were used in this study. These embryos had been donated. for research purposes by the parents and this study complied with the requirements of the Human Embryology and Fertilisation Authority, and the local ethical committee. Frozen embryos were thawed and cultured in Earles balanced salts medium supplemented with 0.4% human serum albumin (Armour Pharmaceuticals UK), until the required developmental stage, then flash frozen in liquid nitrogen in 5 µl of culture fluid (and thus lysed by ice crystals). An identical volume of culture supernatant was frozen as a control. Any remaining cumulus cells were removed during routine handling.

Total RNA from first trimester trophoblast was isolated by the method of Chomsczynski and Sacchi, *Anal. Biochem.*, 162: 156–159 (1987) in which frozen tissue is homogenised in 5 ml of buffer containing 4 M guanidinium thiocyanate (Gibco BRL Livingston, Scotland), 25 mM sodium citrate pH 7.0, 0.5% sarcosyl and 0.1 M 2-mercaptoethanol. The lysate was acidified by the addition of 0.5 ml of 2 M sodium acetate pH 4, and phenol-chloroform extracted using 5 ml of buffer saturated phenol and 1 ml chloroform-isoamylalcohol (49:1 v/v). The suspension was placed on ice for 15 minutes and centrifuged at 10,000 g for 20 minutes at 4° C. The aqueous phase containing RNA was precipitated, washed twice in 70% ethanol, dried and resuspended in TE (10 mM Tris-HCl pH 7.4 and 1 mM EDTA). The concentration of RNA was determined spectrophotometrically at 260 nm.

RNA was prepared from single human embryos using a scaled down protocol based on the above procedure. To assist precipitation of the RNA 100 µg of carrier yeast tRNA (Gibco BRL, Livingston, Scotland) was added at the homogenisation step. The remaining details are as described above, except that all the volumes were 50 fold less and the whole procedure was carried out in 400 µl Eppendorf tubes.

Example 2

Reverse Transcriptase Polymerase Chain Reaction (RT-PCR)

cDNA was synthesised from half the total RNA from each embryo using AMV reverse transcriptase (Super RT, HT Biotech, Cambridge, UK). 3–5 micrograms of RNA was primed with oligo dT (Pharmacia), according to the manufacturers instructions for 60 minutes at 42° C. PCR amplification of the cDNA preparations was performed as previously described (Sharkey, A. et al, *Molecular Endocrinol.*, 6: 1235–1241 (1992)) with a Hybaid Omnigene DNA thermal cycler in a final volume of 30 μl using 1 U of Taq DNA polymerase (Cetus, Emeryville, Ca.) and 10 μM of each of the pair of external primers (see FIG. 4) in the manufacturer's recommended buffer. The following cycle profile was used: 30s at 95° C., 30s at X° C., 30s at 72° C. for 30 cycles, where X is the annealing temperature for each pair of cytokine primers, as shown below.

|         | External Primers (° C.) | Internal Primers (° C.) |
|---------|-------------------------|-------------------------|
| SCF     | 54                      | 54                      |
| HistRNA | 52                      | 59                      |
| c-kit   | 56                      | 56                      |

Oligonucleotide Primers

Oligonucleotide primers for SCF, c-kit and Histidyl-t RNA synthetase were synthesised on a Cruachem PS250 DNA synthesiser. Primer sequences were designed from published nucleotide sequences (see FIG. 4), such that amplification of any contaminating genomic DNA would result in a differently sized product from the cDNA species.

Because of the small amount of material, two pairs of primers were used for each target cDNA, in a nested PCR protocol. One thirtieth of the cDNA products were amplified using Amplitaq (Cetus), in the manufacturers recommended buffer. Following 30 cycles of PCT using the external primer pair, one fiftieth of the first round reaction was transferred to a fresh tube containing the inner primer pair, and subjected to a further 30 rounds of amplification. As negative control, an equal volume of the culture fluid in which the embryo was grown was extracted and subjected to RT-PCR in the same way. Also, 200 cells of the BeWo cell line (ECACC No 86082803) were extracted as positive control.

The primers used in this study are shown in FIG. 4, together with the size of the expected product. The primers depicted include primer A (SEQ ID NO: 7), primer B (SEQ ID NO: 8), primer C (SEQ ID NO: 9), and primer D (SEQ ID NO: 10) for HistRS; primer A (SEQ ID NO: 11), primer B (SEQ ID NO: 12), primer C (SEQ ID NO: 13), and primer D (SEQ ID NO: 14) for SCF; and primer A (SEQ ID NO: 15), primer B (SEQ ID NO: 16), primer C (SEQ ID NO: 17), and primer D (SEQ ID NO: 18) for c-kit. The identity of each product was confirmed by cloning and sequencing as described previously (Sharkey et al, *Mol. Endocrinol.* (1992)). To ensure that the product detected resulted from amplification of cDNA rather than contaminating genomic DNA, primers were chosen to cross intron/lexon boundaries. Ten nanograms of genomic DNA was also subjected to PCR at the same time as the cDNA to verify no product of the expected size resulted from genomic DNA.

RESULTS

The technique of RT-PCR was applied to total RNA extracted from human embryos produced by in vitro fertilisation. Embryos were cultured to the appropriate stage, then quick-frozen in liquid nitrogen. Stored embryos were thawed and total RNA extracted. In order to produce detectable RT-PCR product from total RNA extracted from a single embryo, a nested PCR protocol was employed in which the cDNA was subjected to two sets of PCR amplification with an external primer pair, followed by an internal pair. Primers were based on published cDNA sequences and designed to span intron-exon boundaries so that amplification of contaminating genomic DNA could be readily distinguished from cDNA products.

Initially, cDNA from each embryo was tested with primers for histidyl tRNA synthetase (HistRS) to confirm successful RNA isolation and reverse transcription. The primers used gave rise to weak products of greater than 400 bp from genomic DNA and 110 bp from cDNA derived from HistRS mRNA. Transcripts for Hist RS were detected in mRNA from embryos at all stages of development, as well as in decidua and the choriocarcinoma cell line BeWo, used as positive controls (FIG. 3, lanes p and q respectively). No product was detected in an equal volume of embryo culture supernatant extracted and subjected to RT-PCR in the same way, indicating that there was no contamination of the culture with extraneous cDNA or RNA.

Examples of similar RT-PCR analysis with primers for SCF and c-kit are shown in FIG. 3. Stocks of cDNA were reverse transcribed from each RNA sample on two separate occasions and the PCR assays were repeated twice on each CDNA stock. The results are shown in FIG. 3, which displays the pattern of expression of c-kit and SCF during pre-implantation development. The identity of the PCR fragments of the correct size was confirmed by sequencing of the cloned PCR products. In cases where novel sized products were seen, these were also cloned and sequenced.

For SCF, the predicted fragment is 966 bp. However, the SCF transcripts appeared to show stage-specific differences in size. Upon cloning and sequencing, the new product appeared to arise due to an alternative splicing event which inserts a new exon between exons 3 and 4. The predicted sequence of the novel transcript is shown in FIG. 1. The novel splicing pattern also involves a frameshift, giving a total of 33 new amino acids, before an in frame stop codon in exon 4.

In a similar analysis using primers specific for c-kit, the receptor for SCF showed that c-kit was expressed at most stages of human pre-implantation embryo development. This suggests that the embryo has the ability to respond to SCF throughout this period.

DISCUSSION

Many growth factors have been shown to influence the development of cultured pre-implantation mammalian embryos (for review see Anderson, E. D., *J. Cellular Biochen.*, 53: 280–287 (1993) and Schultz, G. A. and Hevner, S., *Mutat. Res.*, 296: 17–31 (1992)).

However, there is good evidence for species to species differences in expression of growth factor receptors in pre-implantation development. For instance, EGF mRNA is expressed in the pig embryo but has not been found at any stage in mouse pre-implantation embryos (Vaughan et al, *Development*, 116: 663–669 (1992); Rapolee et al, *Science*, 241: 1823–1825 (1988); and Watson, A. J. et al, Biol. Reprod., 50: 725–733 (1994)). Therefore the usefulness of these studies to researchers interested in factors controlling human pre-implantation development is limited. In addition, the specific growth factors and receptors investigated in such studies frequently have been chosen on an ad hoc basis. Both for ethical and practical reasons, such an approach is not suitable for use with human embryos. We have therefore used a nested RT-PCR method which has allowed us to screen for the expression of growth factor and receptor mRNAs in single human pre-implantation embryos. This method has been widely used over the last few years in other species since it is reliable, sensitive and economical in its use of embryo material.

RT-PCR with primers for Histidyl-tRNA synthetase was used on cDNA samples to confirm that cDNA had been successfully prepared from each embryo RNA sample. cDNA specific for this housekeeping gene was successfully detected in cDNA samples made even from a single 2-cell embryo, indicating that the method was sufficiently sensitive for this study.

SCF was expressed at the 2-cell stage, and then reappeared at the 6-cell stage. This is consistent with maternal expression followed by re-expression from the embryos's genome at the 6-cell stage (Braude, P. et al, *Nature*, 332; 459–461 1988)). SCF transcripts appeared to show stage-specific differences in the transcriptor size. On cloning and sequencing, these were found to be due to alternative splicing of the primary transcript. Two of these variants were similar to those published previously (Martin et al, supra and Sharkey, A. et al, *Mol, Endocrino.*, 6: 1235–1241 (1992)), and one was a novel form which predicts a species of SCF with 33 new amino acids at the carboxy terminus. Several variants of SCF are now known, some of which are membrane bound and bioactive. The species expressed by the pre-implantation embryo include those known to be bicactive, and indicates that various forms of SCF can act through c-kit expressed by the embryo, and can affect embryo development at this time.

What is claimed is:

1. DNA encoding SCF which has the following C-terminal amino acid sequence:

Glu Ile Cys Ser Leu Leu Ile Gly Leu Thr Ala Tyr Lys

Glu Leu Ser Leu Pro Lys Arg Lys Glu Thr Cys Arg Ala

Ile Gln His Pro Arg Lys Asp (SEQ ID NO:1).

2. DNA as claimed in claim 1, wherein the C-terminal sequence begins at position 40 in SEQ ID NO:5 of the SCF amino acid sequence (SEQ ID NO:5).

3. DNA as claimed in claim 2, wherein the amino acid sequence at positions 1 to 39 is that shown for positions 1 to 39 in SEQ ID NO:5.

4. DNA as claimed in claim 1 which comprises the following sequence:

```
GAA ATC TGT TCA TTG TTG ATA GGG CTG ACG GCC TAT AAG (SEQ ID NO: 2)
GAA TTA TCA CTC CCT AAA AGG AAA GAA ACT TGC AGA GCA
ATT CAG CAT CCA AGG AAA GAC TGA.
```

5. DNA which hybridizes under stringent conditions to the DNA of SEQ ID NO: 2.

6. A DNA construct comprising DNA as defined in claim 1.

7. SCF encoded by DNA as defined in claim 1.

8. A pharmaceutical formulation comprising a protein as defined in claim 1 and one or more pharmaceutically acceptable carriers and/or excipients.

* * * * *

UNITED STATES PATENT AND TRADEMARK OFFICE
CERTIFICATE OF CORRECTION

PATENT NO.   : 6,177,556 B1
DATED        : January 23, 2001
INVENTOR(S)  : Sharkey et al.

It is certified that error appears in the above-identified patent and that said Letters Patent is hereby corrected as shown below:

Title page,
Item [30], "Foreign Application Priority Data,"
Please delete "9422293" and insert therefor -- 9422293.2 --.
Line 2, please delete "9508618" and insert therefore -- 9508618.7 --.

Column 19,
Line 5, after "GACTGA", please insert -- (SEQ ID NO:2) --.

Column 20,
Line 1, please delete "(SEQ ID NO:2)".

Signed and Sealed this

Eighth Day of January, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

```
Glu Ile Cys Ser Leu Leu Ile Gly Leu Thr Ala Tyr Lys Glu Leu Ser
1               5                   10                  15

Leu Pro Lys Arg Lys Glu Thr Cys Arg Ala Ile Gln His Pro Arg Lys
            20                  25                  30

Asp
```

(2) INFORMATION FOR SEQ ID NO: 2:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

```
GAAATCTGTT CATTGTTGAT AGGGCTGACG GCCTATAAGG AATTATCACT CCCTAAAAGG        60

AAAGAAACTT GCAGAGCAAT TCAGCATCCA AGGAAAGACT GA                         102
```

(2) INFORMATION FOR SEQ ID NO: 3:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: cDNA (ix) FEATURE:
              (A) NAME/KEY: CDS
              (B) LOCATION:1..114

(xi) SEQUENCE DESCRIPTION: SEQ ID NO: 3:

ATG GAT GTT TTG GAA ATC TGT TCA TTG TTG ATA GGG CTG ACG GCC TAT         48
Met Asp Val Leu Glu Ile Cys Ser Leu Leu Ile Gly Leu Thr Ala Tyr
 1               5                  10                  15

AAG GAA TTA TCA CTC CCT AAA AGG AAA GAA ACT TGC AGA GCA ATT CAG         96
Lys Glu Leu Ser Leu Pro Lys Arg Lys Glu Thr Cys Arg Ala Ile Gln
                 20                  25                  30

CAT CCA AGG AAA GAC TGA CAGCTTTGAA AGAGACCTGA TAATGATGCA               144
His Pro Arg Lys Asp *
             35

AGTAGGAACT TGCATGTGCT TGAACCAAGT CATTGT                                180

(2) INFORMATION FOR SEQ ID NO: 4:

(i) SEQUENCE CHARACTERISTICS:
              (A) LENGTH:  37 amino acids
              (B) TYPE: amino acid
              (D) TOPOLOGY: linear (ii) MOLECULE TYPE: protein (xi) SEQUENCE DESCRIPTION: SEQ ID NO: 4:

Met Asp Val Leu Glu Ile Cys Ser Leu Leu Ile Gly Leu Thr Ala Tyr
 1               5                  10                  15

Lys Glu Leu Ser Leu Pro Lys Arg Lys Glu Thr Cys Arg Ala Ile Gln
                 20                  25                  30

His Pro Arg Lys Asp
             35

(2) INFORMATION FOR SEQ ID NO:5:

(i) SEQUENCE CHARACTERISTICS:
              (A) LENGTH: 820 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: sig_peptide
              (B) LOCATION: 17..91

(ix) FEATURE:
              (A) NAME/KEY: CDS
              (B) LOCATION: 17..643

(ix) FEATURE:
              (A) NAME/KEY: mat_peptide
              (B) LOCATION: 92..643

(xi) SEQUENCE DESCRIPTION: SEQ ID NO:5:

AAGCTTGCCT TTCCTT ATG AAG AAG ACA CAA ACT TGG ATT CTC ACT TGC           49
               Met Lys Lys Thr Gln Thr Trp Ile Leu Thr Cys
               -25                 -20                 -15

ATT TAT CTT CAG CTG CTC CTA TTT AAT CCT CTC GTC AAA ACT GAA GGG         97
Ile Tyr Leu Gln Leu Leu Leu Phe Asn Pro Leu Val Lys Thr Glu Gly
             -10                  -5                   1

ATC TGC AGG AAT CGT GTG ACT AAT AAT GTA AAA GAC GTC ACT AAA TTG        145
Ile Cys Arg Asn Arg Val Thr Asn Asn Val Lys Asp Val Thr Lys Leu
              5                  10                  15

-continued

```
GTG GCA AAT CTT CCA AAA GAC TAC ATG ATA ACC CTC AAA TAT GTC CCC      193
Val Ala Asn Leu Pro Lys Asp Tyr Met Ile Thr Leu Lys Tyr Val Pro
    20                  25                  30

GGG ATG GAT GTT TTG CCA AGT CAT TGT TGG ATA AGC GAG ATG GTA GTA      241
Gly Met Asp Val Leu Pro Ser His Cys Trp Ile Ser Glu Met Val Val
35                  40                  45                  50

CAA TTG TCA GAC AGC TTG ACT GAT CTT CTG GAC AAG TTT TCA AAT ATT      289
Gln Leu Ser Asp Ser Leu Thr Asp Leu Leu Asp Lys Phe Ser Asn Ile
                55                  60                  65

TCT GAA GGC TTG AGT AAT TAT TCC ATC ATA GAC AAA CTT GTG AAT ATA      337
Ser Glu Gly Leu Ser Asn Tyr Ser Ile Ile Asp Lys Leu Val Asn Ile
            70                  75                  80

GTG GAT GAC CTT GTG GAG TGC GTG AAA GAA AAC TCA TCT AAG GAT CTA      385
Val Asp Asp Leu Val Glu Cys Val Lys Glu Asn Ser Ser Lys Asp Leu
            85                  90                  95

AAA AAA TCA TTC AAG AGC CCA GAA CCC AGG CTC TTT ACT CCT GAA GAA      433
Lys Lys Ser Phe Lys Ser Pro Glu Pro Arg Leu Phe Thr Pro Glu Glu
        100                 105                 110

TTC TTT AGA ATT TTT AAT AGA TCC ATT GAT GCC TTC AAG GAC TTT GTA      481
Phe Phe Arg Ile Phe Asn Arg Ser Ile Asp Ala Phe Lys Asp Phe Val
115                 120                 125                 130

GTG GCA TCT GAA ACT AGT GAT TGT GTG GTT TCT TCA ACA TTA AGT CCT      529
Val Ala Ser Glu Thr Ser Asp Cys Val Val Ser Ser Thr Leu Ser Pro
                135                 140                 145

GAG AAA GAT TCC AGA GTC AGT GTC ACA AAA CCA TTT ATG TTA CCC CCT      577
Glu Lys Asp Ser Arg Val Ser Val Thr Lys Pro Phe Met Leu Pro Pro
            150                 155                 160

GTT GCA GCC AGC TCC CTT AGG AAT GAC AGC AGT AGC AGT AAT AGT AAG      625
Val Ala Ala Ser Ser Leu Arg Asn Asp Ser Ser Ser Ser Asn Ser Lys
            165                 170                 175

TAC ATA TAT CTG ATT TAA TGCATGCATG GCTCCAATTA GCACCTATAG             673
Tyr Ile Tyr Leu Ile *
180

GAGTATTGCA TGGGCTTTCA AGGAAACTTC TACATTTATT ATTATTGATA CTGTTCTGTT    733

ACTGTTATTC CTTTTATGGT CTTCTTGAGA CTTAAGTTTG TAGAATTAAA TTTCCCTAGA    793

GCTGGAGATA ATGTTTAGAG AATTAGG                                       820

(2) INFORMATION FOR SEQ ID NO:6:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO:6:

Met Lys Lys Thr Gln Thr Trp Ile Leu Thr Cys Ile Tyr Leu Gln Leu
-25                 -20                 -15                 -10

Leu Leu Phe Asn Pro Leu Val Lys Thr Glu Gly Ile Cys Arg Asn Arg
                -5                   1                   5

Val Thr Asn Asn Val Lys Asp Val Thr Lys Leu Val Ala Asn Leu Pro
            10                  15                  20

Lys Asp Tyr Met Ile Thr Leu Lys Tyr Val Pro Gly Met Asp Val Leu
            25                  30                  35

Pro Ser His Cys Trp Ile Ser Glu Met Val Val Gln Leu Ser Asp Ser
40                  45                  50                  55

Leu Thr Asp Leu Leu Asp Lys Phe Ser Asn Ile Ser Glu Gly Leu Ser
                60                  65                  70
```

```
Asn Tyr Ser Ile Ile Asp Lys Leu Val Asn Ile Val Asp Asp Leu Val
             75                  80                  85

Glu Cys Val Lys Glu Asn Ser Ser Lys Asp Leu Lys Lys Ser Phe Lys
         90                  95                 100

Ser Pro Glu Pro Arg Leu Phe Thr Pro Glu Glu Phe Arg Ile Phe
    105                 110                 115

Asn Arg Ser Ile Asp Ala Phe Lys Asp Phe Val Val Ala Ser Glu Thr
120                 125                 130                 135

Ser Asp Cys Val Val Ser Ser Thr Leu Ser Pro Glu Lys Asp Ser Arg
            140                 145                 150

Val Ser Val Thr Lys Pro Phe Met Leu Pro Pro Val Ala Ala Ser Ser
            155                 160                 165

Leu Arg Asn Asp Ser Ser Ser Ser Asn Ser Lys Tyr Ile Tyr Leu Ile
            170                 175                 180
```

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

CCGCAGGTCG AGACAGC                                         17

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

CAAACACCTT CTCGCGAA                                       18

(2) INFORMATION FOR SEQ ID NO: 9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

CTTCAGGGAG AGCGCGTGC                                     19

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

TCATCAGGAC CCAGCTGTGC                                                    20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

CAATGCGTGG ACTATCTGCC                                                    20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

GTTCTAAATG AGACCCAAGT                                                    20

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

AACAGCTAAA CGGAGTCGCC                                                    20

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

ACAGTGTTGA TACAAGCCAC                                                    20

(2) INFORMATION FOR SEQ ID NO: 15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

GAAGTACAGT GGAAGGTTGT T                                                  21

```
(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

CATCGGCCAC TAAAGTGTGC T                                          21

(2) INFORMATION FOR SEQ ID NO: 17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

GGTTGTTGAG GCAACTGCTT A                                          21

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

GGTGACCCAA ACACTGATTC                                            20
```